United States Patent
Wohland et al.

(10) Patent No.: US 7,468,518 B2
(45) Date of Patent: Dec. 23, 2008

(54) FLUORESCENCE CORRELATION SPECTROSCOPY WITH SINGLE EXCITATION WAVELENGTH

(75) Inventors: Thorsten Wohland, Singapore (SG); Ling Chin Hwang, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 10/576,889

(22) PCT Filed: Oct. 22, 2004

(86) PCT No.: PCT/SG2004/000349

§ 371 (c)(1), (2), (4) Date: Jan. 22, 2007

(87) PCT Pub. No.: WO2005/040771

PCT Pub. Date: May 6, 2005

(65) Prior Publication Data

US 2007/0215815 A1 Sep. 20, 2007

Related U.S. Application Data

(60) Provisional application No. 60/513,195, filed on Oct. 23, 2003.

(51) Int. Cl.
G01N 21/64 (2006.01)

(52) U.S. Cl. .................................. 250/458.1
(58) Field of Classification Search .............. 250/458.1
See application file for complete search history.

(56) References Cited

U.S. PATENT DOCUMENTS

| 4,745,285 | A | 5/1988 | Recktenwald et al. .... 250/458.1 |
| 5,815,262 | A | 9/1998 | Schrof et al. ................. 356/318 |
| 6,008,373 | A | 12/1999 | Waggoner et al. ........... 548/427 |
| 6,130,094 | A | 10/2000 | Waggoner et al. ............. 436/63 |
| 6,177,247 | B1 | 1/2001 | Mathies et al. .................. 435/6 |
| 6,200,818 | B1 | 3/2001 | Eigen et al. ................. 436/172 |
| 6,384,914 | B1 | 5/2002 | Drexhage et al. ........... 356/318 |
| 2002/0064789 | A1 | 5/2002 | Weiss et al. ..................... 435/6 |

(Continued)

FOREIGN PATENT DOCUMENTS

WO 02/08732 1/2002

(Continued)

OTHER PUBLICATIONS

Hwang et al., Dual-Color Fluorescence Cross-Correlation Spectroscopy Using Single Laser Wavelength Excitation, ChemPhysChem 2004, pp. 549-551.

(Continued)

*Primary Examiner*—David P Porta
*Assistant Examiner*—Marcus H Taningco
(74) *Attorney, Agent, or Firm*—Allen, Dyer, Doppelt, Milbrath & Gilchrist, P.A.

(57) ABSTRACT

At least two fluorophores (e.g. fluorescein-biotin and tetramethylrhodamine-streptavidin conjugate) for use in fluorescence correlation spectroscopy, characterized in that the fluorophores have substantially the same excitation wavelength (a) and different emission wavelengths (b and d). The fluorophores are used for simultaneous excitation with a single laser wavelength in fluorescence cross-correlation spectroscopy (FCCS). The central wavelength (c) of the dichroic mirror used for the separation of the emission signal lies between the emission wavelengths of the fluorophores.

15 Claims, 10 Drawing Sheets

U.S. PATENT DOCUMENTS

| | | | |
|---|---|---|---|
| 2003/0032054 A1* | 2/2003 | Colyer et al. | 435/7.1 |
| 2003/0203407 A1* | 10/2003 | Craig et al. | 435/7.1 |
| 2004/0022684 A1* | 2/2004 | Heinze et al. | 422/82.08 |
| 2005/0260593 A1* | 11/2005 | Kumar et al. | 435/6 |

FOREIGN PATENT DOCUMENTS

| | | |
|---|---|---|
| WO | 02/40978 | 5/2002 |
| WO | 03/003015 | 1/2003 |

OTHER PUBLICATIONS

Elson et al., Fluorescene Correlation Spectroscopy, vol. 13, 1-27, 1974.

Rigler et al., Fluorescence Correlation Spectroscopy with High Count Rate and Low Background: Analysis of Translational Diffusion, European Biophysics Journal, 1993.

Meseth et al., Resolution of Fluorescence Correlation Measurements, Biophysical Journal, vol. 76, Mar. 1999, pp. 1619-1631.

Schwille et al., Dual-Color Fluorescence Cross-Correlation Spectroscopy for Multicomponent Diffusional Analysis in Solution, Biophysical Journal, vol. 72, Apr. 1997, pp. 1878-1886.

Thompson et al., Recent Advances in Fluorescence Correlation Spectroscopy, Current Opinion in Structural Biology 2002, pp. 634-641.

Heinze et al., Simultaneous Two-Photon Excitation of Distinct Labels for Dual-Color Fluorescence Crosscorrelation Analysis, PNAS, Sep. 12, 2000, vol. 97, No. 19, pp. 10377-10382.

Krichevsky et al., Fluorescence Correlation Spectroscopy: The Technique and its Applications, Reports on Progress in Physics 65, 2002, pp. 251-297.

Heinze et al., Triple-Color Coincidence Analysis: One Step Further in Following Higher Order Molecular Complex Formation, Biophysical Journal, vol. 86, Jan. 2994, pp. 506-516.

Alivisatos, Semiconductor Clusters, Nanocrystals, and Quantum Dots, Science, New Series, vol. 271, No. 5251, Feb. 16, 1996, pp. 933-937.

Weidemann et al., Analysis of Ligand Binding by Two-Colour Fluorescence Cross-Correlation Spectroscopy, Single Molecules 3, 2002, pp. 49-61.

Aragón et al., Fluorescence Correlation Spectroscopy as a Probe of Molecular Dynamics, The Journal of Chemical Physics, vol. 64, No. 4, Feb. 15, 1976.

Tuk et al., Solving Inconsistencies in the Analysis of Receptor-Ligand Interactions, TiPS, Nov. 1996, vol. 17.

Gruber et al., Accurate Titration of Avidin and Streptavidin with Biotin—Fluorophore Conjugates in Complex, Colored Biofluids, Biochimica et Biophysica Acta 1381, 1998, pp. 203-212.

Kada et al., Rapid Estimation of Avidin and Streptavidin by Fluorescence Quenching or Fluorescence Polarization, Biochimica et Biophysica Acta 1427, 1999, pp. 44-48.

Glazer et al., Fluorescent Tandem Phycobiliprotein Conjugates, Biophysics Journal, vol. 43, Sep. 1983, pp. 383-386.

Hulme et al., Strategy and Tactics in Receptor-Binding Studies, Chapter 4, pp. 63-69 and 86-93, Oxford University Press, Receptor-Ligand Interactions: A Practical Approach.

* cited by examiner

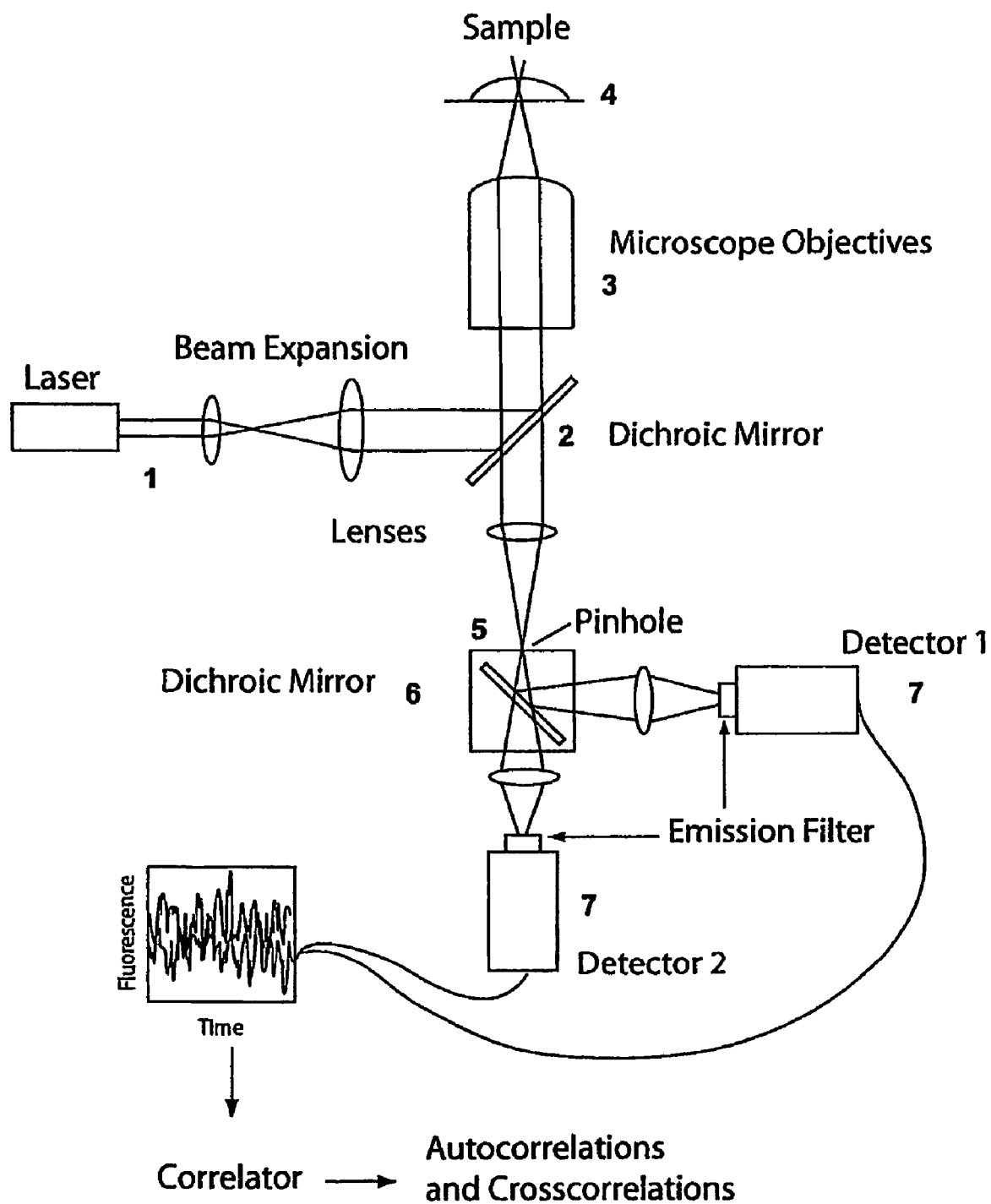

FLUORESCENCE CORRELATION SPECTROSCOPY WITH SINGLE EXCITATION WAVELENGTH

This application claims priority under Article 8 of the Patent Cooperation Treaty of U.S. application 60/513,195, filed on Oct. 23, 2003 the entire contents of which are hereby incorporated by reference.

BACKGROUND OF THE INVENTION

1. Field of the Invention

The invention relates to fluorescence correlation spectroscopy, especially to multicolor cross-correlation spectroscopy, in which the invention can be used to detect interactions between molecules where all the molecules have been labeled with fluorophores that can be excited simultaneously with one laser wavelength but have different emission characteristics.

2. Description of the Related Art

Fluorescence Correlation Spectroscopy (FCS) is a technique that can determine the characteristics of molecular processes by measuring fluorescence fluctuations in a small sample volume (typically a confocal volume) that are caused by the molecular processes. Typical related art FCS technology is described by E. L. Elson and D. Magde (Fluorescence Correlation Spectroscopy. I. Conceptual basis and theory. *Biopolym.* 13:1-27, 1974) and R. Rigler, U. Mets, J. Widengren, and P. Kask (Fluorescence Correlation Spectroscopy with High Count Rate and Low-Background—Analysis of Translational Diffusion. *Eur. Biophys. J.* 22 (3):169-175, 1993).

FCS uses only one fluorescent label and is limited in its resolution, and FCS can resolve two processes only when their characteristic times are different by at least a factor 1.6 to 2 (see U. Meseth, T. Wohland, R. Rigler, and H. Vogel. Resolution of Fluorescence Correlation Measurements. *Biophys. J.* 76:1619-1631, 1999).

Fluorescence Cross-correlation Spectroscopy (FCCS) is also a technique that allows the measurement of association events of two differently fluorescently labeled particles by detecting their distinct signals from an observation volume in at least two detectors (see P. Schwille, F J Meyer-Almes, and Rudolf Rigler. Dual-Color Fluorescence Cross-Correlation Spectroscopy for Multicomponent Diffusional Analysis in Solution. *Biophys. J.* 72 (April):1878-1886, 1997). The detector signals are cross-correlated and conclusions can be drawn about the association/correlation of the two particles. This technique circumvents the resolution limitations of FCS and can measure any kind of association independent of whether the association changes the molecular process sufficiently. For example, the association does not have to change a molecular process (e.g., diffusion) by a factor of 2 to be measured (for diffusion that means a factor 8 in mass change). However, to achieve the excitation of two fluorophores that have emission characteristics that are sufficiently different to allow separate detection of the two fluorophores, FCCS requires the use of two different laser wavelengths and thus the necessitates the alignment of two laser beams to the same spot in a microscope. This procedure is difficult and has blocked the commercial and scientific exploitation of this technique (see M. Rarbach, U. Kettling, A. Koltermann, and M. Eigen, Dual-color fluorescence cross-correlation spectroscopy for monitoring the kinetics of enzyme-catalyzed reactions. *Methods* 24 (2):104-116, 2001; N. L. Thompson, A. M. Lieto, and N. W. Allen. Recent advances in fluorescence correlation spectroscopy. *Current Opinion in Structural Biology* 12 (5):634-641, 2002).

Recently, it was shown that FCCS can be performed with a single laser beam when two-photon excitation is used (see K. G. Heinze, A. Koltermann, and P. Schwille, Simultaneous two-photon excitation of distinct labels for dual-color fluorescence crosscorrelation analysis, *Proceedings of the National Academy of Sciences of the United States of America;* 97 (19):10377-10382, 2000). The costs of the system and problems of finding fluorophores with adequate two-photon absorption cross sections limit this technique (see O. Krichevsky, G. Bonnet, Fluorescence correlation spectroscopy: the technique and its applications, Rep. Prog. Phys. 65, 251-297, 2002).

It has been suggested that fluorophores with large Stokes' shifts can be used for simultaneous excitation with a single laser beam but no appropriate system has been suggested up to now (see, e.g., K. G. Heinze, M. Jahnz, P. Schwille. Triple Color Coincidence Analysis: One Step Further in Following Higher Order Molecular Complex Formation. Biophys. J. 86, 506-516, 2004). While the related art has found that no appropriate dyes have been found that fulfill the condition for single laser line excitation and emission in two different wavelength ranges. However, a single laser line excitation has recently been demonstrated by two-photon excitation, but no single laser line one photon excitation is found. The first demonstration of single laser line one photon excitation for dual color fluorescence cross correlation in an article published by the inventors (see L. C. Hwang and T. Wohland. Dual-Color Fluorescence Cross-Correlation Spectroscopy Using Single Laser Wavelength Excitation, Chem Phys Chem 5, 549-551, 2004).

FCS and FCCS instruments are commercially available (Carl Zeiss and Olympus). However, they use two laser beams for the excitation of their samples. Alternatively, a single laser for two-photon excitation can be used (IR, pulsed laser).

At least two patents (U.S. Pat. Nos. 6,200,818 and 6,582,903) have claimed the excitation of fluorophores with one single wavelength and their detection in different detection channels due to different Stokes shifts of the fluorophores. However, both patents fail to set forth a system fulfilling the conditions for such measurements.

As a result, at least preferred embodiments of the present invention seek to facilitate fluorescence cross-correlation spectroscopy that uses a single laser wavelength.

SUMMARY OF THE INVENTION

In accordance with a first aspect of the present invention there are provided at least two fluorophores for use in fluorescence correlation spectroscopy, characterized in that the fluorophores have substantially the same excitation wavelength and different emission wavelengths.

In accordance with a second aspect of the present invention there is provided a screening method for at least two binding partners, which comprises: labeling each binding partner with a fluorophore, characterized in that the at least two fluorophores have substantially the same excitation wavelength and different emission wavelengths.

One of the fluorophores may have a larger Stokes shift than the other. A relative Stokes shift difference between the fluorophores may be greater than about 40 nm. The relative Stokes shift difference between the fluorophores may be greater than about 100 nm.

At least one of the fluorophores may comprise a nanocrystal or a quantum dot. At least one of the fluorophores may comprise a fluorescent energy transfer dye. At least one of the fluorophores may comprise a standard organic dye.

The fluorophores may comprise fluorescein and quantum red. The fluorophores may comprise fluorescein and tetramethylrhodamine. The fluorophores may comprise fluorescein and semiconductor nanocrystals. The fluorophores may comprise 3 or more fluorophores.

The binding partners may have a mass difference of less than a factor of 10. The binding partners may have a mass difference of less than a factor of 8. The binding partners may comprise biotin and streptavidin.

In accordance with a third aspect of the present invention there provided a biological screening apparatus, comprising: a single laser beam source; a optical system for directing the single laser beam onto a sample and for directing fluorescence emitted from the sample towards a spectrograph unit; the spectrograph unit separating the emitted fluorescence by wavelength; and a detector unit for detection of the fluorescence at respective different wavelengths.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

FIG. 2 shows excitation and detection pathways for the simultaneous detection of two wavelength ranges in an example embodiment.

DETAILED DESCRIPTION

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Fluorophores have characteristic excitation wavelengths and emit light at a longer wavelength. The difference between the maximum excitation wavelength and maximum emission wavelength is called the Stokes shift. Up to now no fluorophore combination of two or more fluorophores has been proposed that can be excited at one single laser wavelength but whose Stokes shifts are sufficiently different to allow the detection of the emission of the two fluorophores in different channels.

The invention allows the use of fluorescence energy transfer dyes, i.e. dyes that are composed of a donor and acceptor fluorophore, which can transfer excitation energy from one dye to another, by a radiationless process. In these dyes the donor fluorophore is excited. Since the emission spectrum of the donor is overlapping with the excitation spectrum of the acceptor, energy transfer between the two dyes is possible. Emission of the fluorescence energy transfer dye takes then place at the emission wavelength of the acceptor dye. The Stokes shift of these dyes can thus reach 100 nm.

In an additional embodiment of the invention, semiconductor nanocrystals or quantum dots can be excited at any wavelength below a certain threshold wavelength, and their emission characteristics depend on their size. By choosing an excitation wavelength that is sufficiently low, a large difference between excitation and emission can be achieved.

Using any of these two or more fluorophores in combination with fluorophores of smaller Stokes shift but similar excitation characteristics allows the simultaneous excitation of both with a single laser wavelength and at the same time the detection of their particular emission wavelength in different detectors. These fluorophore pairs (large and small Stokes shift fluorophore) are ideal labels for FCCS measurements that can be performed with a single laser wavelength.

Under certain circumstances this method can be used for combinations of small standard organic dyes (e.g. tetramethylrhodamine and fluorescein), which are in common usage. This extension to standard dyes broadens the application of this invention considerably, and the labeling process is not restricted to the specialized dyes described above. The limits for application of the invention are only bound by the theoretical limits of the cross-correlation function (CCF).

Figure 1A:
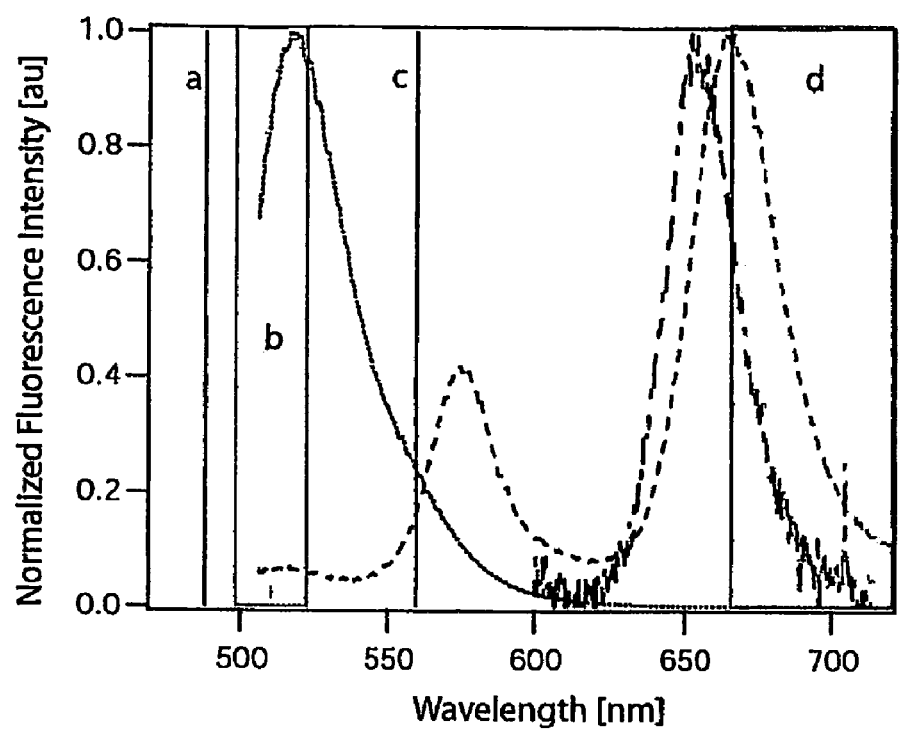
FIGS. 1A and 1B show normalized emission spectra of dyes in an example embodiment.

FIG. 1A shows the normalized emission spectra of an organic dye (fluorescein-biotin, ITS Science & Medical Pte Ltd., Singapore, dotted line), a fluorescence energy transfer dye (Quantum Red, SIGMA-Aldrich Pte Ltd., Singapore, dashed line), and a semiconductor nanocrystal (QD655, Quantum Dot Corp., CA, USA, dot-dash line). FIG. 1A shows the laser excitation wavelength (a), the emission filter transmission range for detector 1 (b), the dichroic mirror center wavelength for the separation of the emission light into detector 1 and 2 (c), and the emission filter transmission range for detector 2 (d). FIG. 1A is an example of how small Stokes shift organic dyes can be used in combination with large Stokes shift fluorescence energy transfer dyes or semiconductor nanocrystals for simultaneous excitation with a single laser wavelength in FCCS.

Figure 1B:
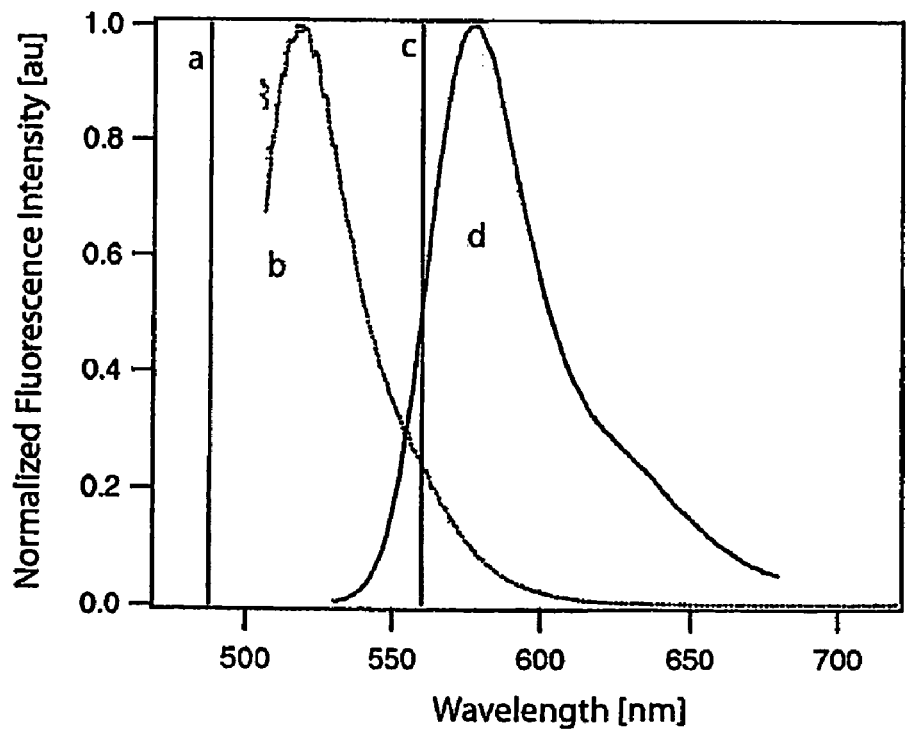

FIG. 1B is similar to FIG. 1A, but with the emission spectra of two organic dyes BF (fluorescein-biotin, ITS Science & Medical Pte Ltd., Singapore, dotted line) and TMRSA (Tetramethylrhodamine-streptavidin conjugate, Molecular Probes, Eugene, USA).

FIG. 2: shows a spectroscopic apparatus having an excitation and detection pathway for simultaneous detection of two wavelength ranges. A single laser beam 1 is coupled over a dichroic mirror 2 and a microscope objective 3 to a sample 4. Fluorescence excited by the laser beam and emitted from the sample 4 is spatially filtered by a pinhole 5. The emission light is then separated by wavelength by a dichroic mirror 6 and detected on two or more different detectors 7, which can use optical filters to further restrict the wavelength range of detection. The light from the filters is then auto- and cross-correlated.

Figure 3A:
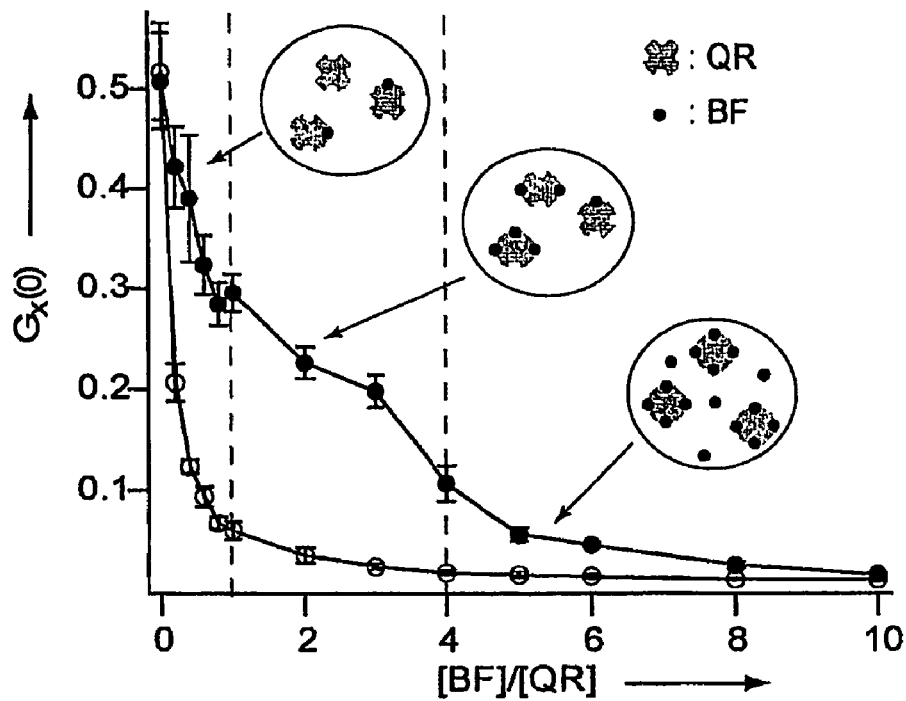
FIGS. 3A and 3B show binding curves for streptavidin and biotin in an example embodiment.
Figure 3B:
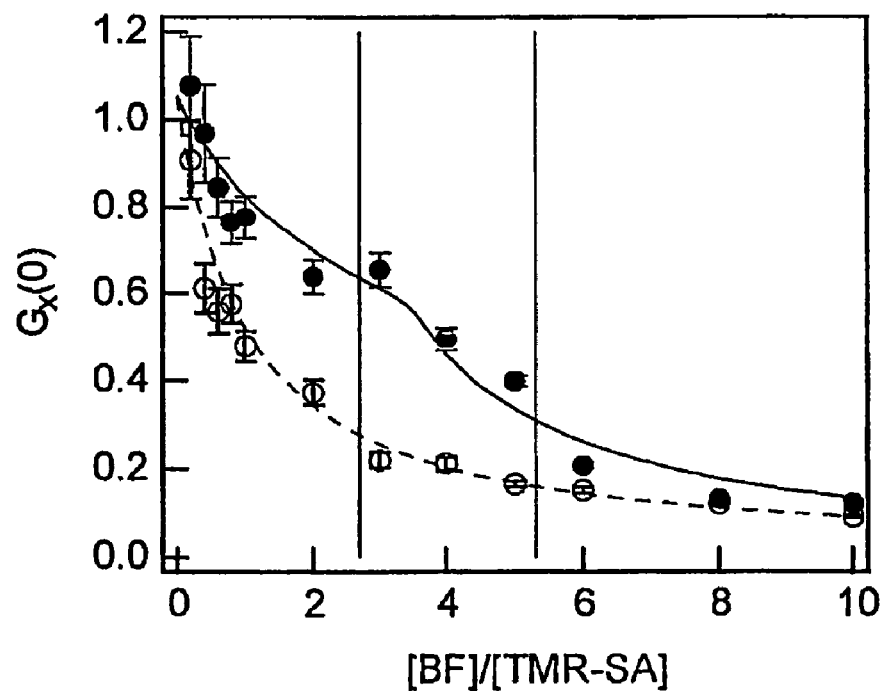

FCCS with single laser wavelength excitation was performed using the apparatus in FIG. 2. Results are shown in FIGS. 3A and 3B. The laser beam 1 is coupled into the microscope objective 3 by means of a dichroic mirror 2 and focused into a sample 4. The large and small Stokes shift fluorophores in the sample are excited, their emission is collected by the microscope objective 3, passes the dichroic mirror 2, which separates the excitation and emission light, and is spatially filtered by a pinhole 5 (confocal principle). The emission light is then separated by a second dichroic mirror 6 into the distinct emissions from the large and small Stokes shift fluorophores. The detector signals are the auto- and cross-correlated to yield information on the interaction of the fluorescently labeled particles.

Results for an example of the application of the invention is shown in FIG. 3A. FIG. 3A shows a binding curve (full circles) recorded for streptavidin and biotin binding in which biotin was labeled with fluorescein (fluorescein-biotin) and streptavidin with a energy transfer dye (Streptavidin Quantum Red conjugate, SIGMA-Aldrich Pte Ltd., Singapore), and a negative control (empty circles) in which binding of the fluorescence labeled molecules was suppressed by an excess of unlabeled biotin (Amersham Bisosciences Ltd., Singapore). The y-axis denotes N as defined as the cross-correlation function (CCF) $G_x(0)$, and the x-axis is the ratio of the concentration of biotin-fluorescein to quantum-red.

FIG. 3B shows the binding between streptavidin and biotin. In this case biotin was labeled with fluorescein (fluorescein-biotin) and streptavidin with tetramethylrhodamine (TMRSA). The positive control (binding) is depicted as full circles, the negative control (with excess unlabeled biotin to suppress BF binding) as empty circles.

Figure 4:
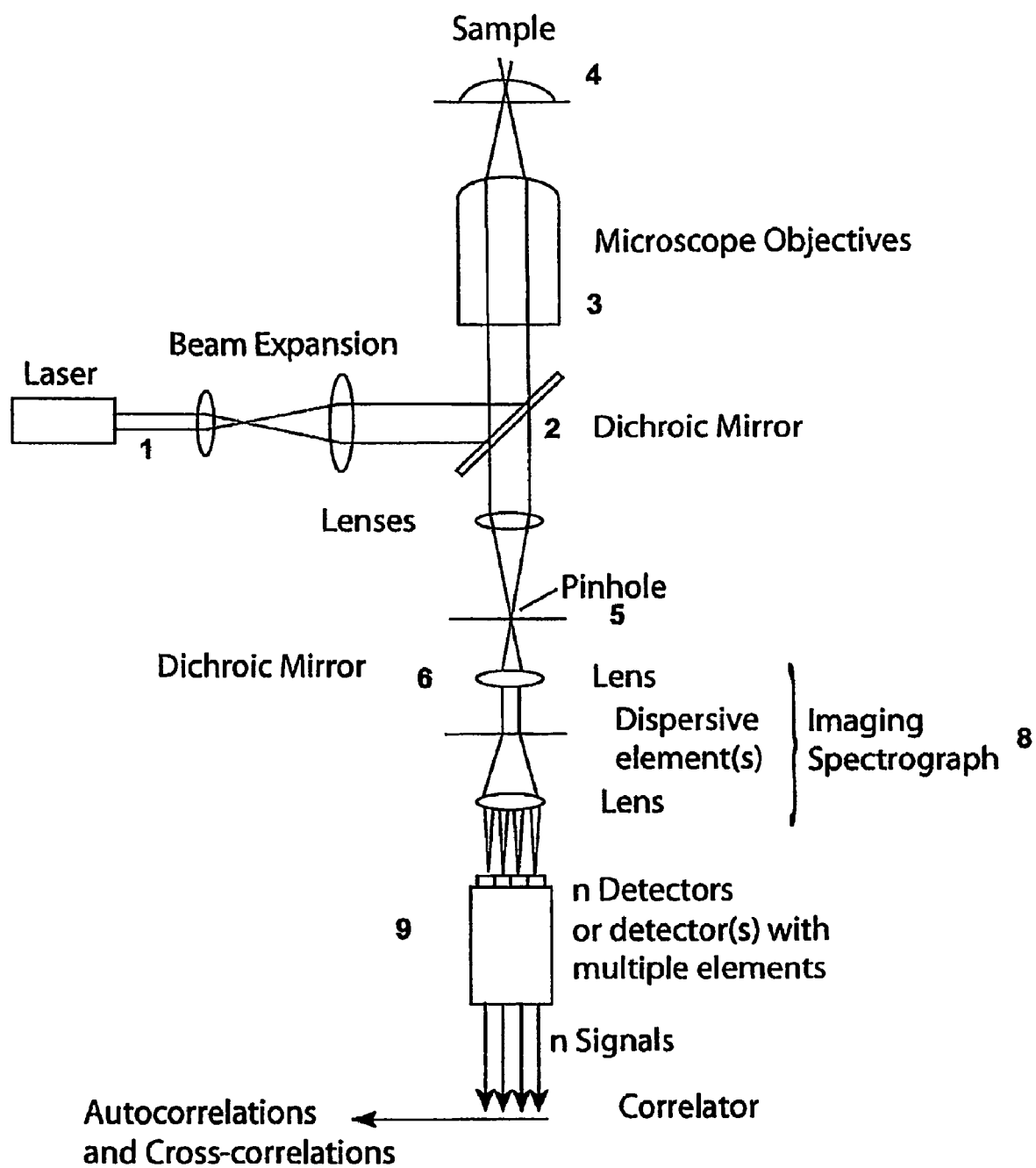
FIG. 4 shows excitation and detection pathways for the simultaneous detection of two wavelength ranges after passage through a pinhole in an example embodiment.

FIG. 4 shows a spectroscopic apparatus similar to FIG. 2, but after passage through the pinhole 5, the emission light is separated according to wavelength by an imaging spectrograph 8 (a set of lenses and a dispersive element or, in an alternative embodiment, by several dichroic mirrors) and detected by several detectors 9. From the signal of the detectors all auto- and cross-correlation functions can be calculated. In FIG. 4, the dispersive element separates the detected light according to wavelength. The emission light will then be detected on a range of detectors or a detector with multiple elements that are closely spaced (or contiguous). Each detector (or detector element) will measure a different part of the wavelength spectrum. The signals from the different detectors can either be treated individually or can be mutually added to create signals for larger parts of the spectrum. The resulting signals can then be autocorrelated and/or mutually cross-correlated. This invention allows the measurement of more than two distinct wavelength ranges in the emission light and has the capability of adjusting the different wavelength ranges in their extent.

Theory of Cross-Correlation Function (CCF)

In this section we first derive a general expression for the CCF. A normalized general expression for CCF is given by $$G_x(\tau) = \frac{\langle \delta F_1(t) \delta F_2(t+\tau) \rangle}{\langle F_1(t) \rangle \langle F_2(t) \rangle} = \frac{\langle F_1(t) F_2(t+\tau) \rangle}{\langle F_1(t) \rangle \langle F_2(t) \rangle} - 1. \quad (1)$$

where $F_i(t)$ denotes the fluorescence intensity detected in either of the two detection channels at a time t, $\tau$ is the correlation time, and the angular brackets denote the time average. $\delta F_i(t)$ denotes the fluctuations of the fluorescence signal around its time averaged mean values $\langle F_i(t) \rangle$, and thus $F_i(t) = \langle F_i(t) \rangle + \delta F_i(t)$. For the case of differently labeled ligand and receptor particles, which are detected in two different channels, the fluorescence in the different channels i is given by:

$$F_i(t) = \eta_{Li} c_L + \sum_{n*} \eta_{Ln*i} c_{Ln*} + \eta_{Ri} c_R + \sum_{n*} (\eta_{Ln*Ri} + \eta_{RLn*i}) c_{RLn*}. \quad (2)$$

The different fluorescent yields (counts per particle and second) in channel i are defined as follows:

$\eta_{Li}$: fluorescence yield of unbound labeled ligand
$\eta_{Ri}$: fluorescence yield of unbound labeled receptor
$\eta_{Ln*i}$: fluorescence yield of unlabeled receptor with n* labeled ligands L bound
$\eta_{Ln*Ri}$: fluorescence yield of n* labeled ligands L in a ligand receptor complex
$\eta_{RLn*i}$: labeled receptor R in a ligand receptor complex with n* fluorescent ligands These different fluorescence yields $\eta$ have to be included to account for the fluorescence of single and multiply labeled complexes, quenching effects (upon labeling or upon binding) and possible fluorescence resonance energy transfer (FRET) in the different ligand-receptor complexes. For a solution of the whole CCF a characteristic time dependent process (diffusion, flow etc.) has to be assumed. In the invention, we concentrate only on the amplitudes of the CCF, but the extension to the full CCF is straightforward and the solutions have been previously published (see Weidemann, T., Wachsmuth, M., Tewes, M., Rippe, K., and Langowski, J., Single Mol. 3(1), 49 (2002)).

Putting equation 2 into equation 1, accounting for 2 detection channels, and assuming a focal intensity profile that is Gaussian in all three axes allows the CCF can be calculated (see Aragon, S. R. and Pecora, R., J. Chem. Phys. 64(4), 1791 (1976); Elson, E. L. and Magde, D., Biopolym. 13, 1 (1974)).

$$G_x(0) = \frac{\eta_{L1}\eta_{L2} c_L + \sum_{n*} \eta_{Ln*1}\eta_{Ln*2} c_{Ln*} + \eta_{R1}\eta_{R2} c_{R_v} + \sum_{n*} (\eta_{Ln*R1} + \eta_{RLn*1})(\eta_{Ln*R2} + \eta_{RLn*2}) c_{RLn*}}{V_{eff} N_A \left[ \left( \eta_{L1} c_L + \sum_{n*} \eta_{Ln*1} c_{Ln*} + \eta_{R1} c_{R_v} + \sum_{n*} (\eta_{Ln*R1} + \eta_{RLn*1}) c_{RLn*} \right) * \left( \eta_{L2} c_L + \sum_{n*} \eta_{Ln*2} c_{Ln*} + \eta_{R2} c_{R_v} + \sum_{n*} (\eta_{Ln*R2} + \eta_{RLn*2}) c_{RLn*} \right) \right]}. \quad (3)$$

For the negative control, i.e. no binding, the equation simplifies to $$G_x^-(0) = \frac{\eta'_{L1}\eta'_{L2}{}^* L_t + \eta'_{R1}\eta'_{R2}{}^* R_t}{V_{eff} N_A (\eta'_{L1}{}^* L_t + \eta'_{R1}{}^* R_t)(\eta'_{L2}{}^* L_t + \eta'_{R2}{}^* R_t)} \quad (4)$$

where the $\eta'$ represent the fluorescence yields of the different species in the presence of the competitor for the negative control.

For the data collected in this work the standard deviation of the amplitude of the CCFs is on the order of $\Delta=10\%$ or lower. To detect binding we demand that the difference between positive and negative control differs by at least 6 standard deviations, i.e.

$$G_x(0)-G_x^-(0) \geq 3\Delta \cdot (G_x(0)+G_x^-(0)) \quad (5).$$

This demand can be expressed in an inequality $$R \equiv \frac{G_x(0)}{G_x^-(0)} \frac{1-3\Delta}{1+3\Delta} \geq 1, \quad (6)$$

where we define the detection threshold R as the left hand side of Eq. 6. The positive and negative control in SW-FCCS can thus only be distinguished when inequality 6 is fulfilled. The ratio R depends on several parameters, in particular on the purity of receptor and ligand, on quenching of receptor and ligand upon binding, on non-specific binding, and on the fluorescence yields of ligand, receptor, and ligand receptor complex (as measured in the setup).

Calculations of SW-FCCS Limits

For calculations of limits of the $K_d$ which can be determined with SW-FCCS (single wavelength fluorescence cross-correlation spectroscopy), the ratio R was calculated in dependence of different parameters. Since the solution for the binding curve (and the detection threshold R) is constant for constant ratios of $L_t/R_t$ and $K_d/R_t$, all results are given in terms of these dimensionless parameters.

According to Eq. 6 the ratio R must be at least 1 to allow the distinction between positive and negative control. In Table 2 we show the maximum values for $K_d/R_t$ at which R=1 and report the corresponding value of $L_t/R_t$ at which this maximum is reached (see supplement for graphs depicting the R=1 line for different conditions). With the knowledge that FCS measurements can be performed at fluorophore concentrations between about 0.1 nM and 1 μM, one can directly calculate possible $K_d$s accessible by this technique and the ideal receptor and ligand concentrations to be employed. In these calculations we assumed i) a standard deviation of $\Delta=10\%$ for all measurements, ii) that quenching upon binding is always equal in both detection channels, and iii) that there is no quenching for negative controls.

Condition i) was found to be generally fulfilled in the measurements. In FCS the amplitude can often be determined with a much lower standard deviation. Condition ii) might improve or worsen the resolution limit since it can result in larger or smaller differences for the fluorescence yield products for the different species. Condition iii) would in general worsen the resolution limit since more quenching means lower signal to noise ratio in the SW-FCCS measurements.

One has to differentiate between two different cases:

1) If $\frac{L_t}{R_t} \geq 1$, then $R_t^{\max} = \frac{R_t}{L_t} * 10^{-6} M$ and $R_t^{\min} = \frac{R_t}{L_t} * 10^{-10} M$.

2) If $\frac{L_t}{R_t} < 1$, then $R_t^{\max} = 10^{-6} M$ and $R_t^{\min} = 10^{-10} M$.

The maximum and minimum $K_d$s can be calculated by $$K_d^{\max} = \frac{K_d}{R_t} R_t^{\max} \quad \text{and} \quad (7a)$$

$$K_d^{\min} = \frac{K_d}{R_t} R_t^{\min}. \quad (7b)$$

Receptor-Ligand Complexes

The samples used in SW-FCCS binding studies are ligands and receptors, which are labeled with different fluorophores, with total concentrations $L_t$ and $R_t$, respectively. Due to the labeling process both samples will contain i) total active labeled ligands and receptors (*$L_t^+$ and *$R_t^+$), ii) total inactive labeled ligands and receptors (*$L_t^-$ and *$R_t^-$, comprising all fluorescent non-active particles), iii) total unlabeled active ligands and receptors ($^0L_t^+$ and $^0R_t^+$), and iv) total unlabeled non-active ligands and receptors ($^0L_t^-$ and $^0R_t^-$).

$$L_t = *L_t^+ + *L_t^- + {}^0L_t^+ + {}^0L_t^- \quad (8a)$$

$$R_t = *R_t^+ + *R_t^- + {}^0R_t^+ + {}^0R_t^- \quad (8b)$$

The signal in SW-FCCS will be determined by the fluorescent particles (*$L_t^+$, *$L_t^-$, *$R_t^+$, *$R_t^-$), but binding will be determined by the active particles (*$L_t^+$, $^0L_t^+$, *$R_t^+$, $^0R_t^+$). Thus inactive labeled particles (*$L_t^-$, *$R_t^-$) will increase the background for SW-FCCS measurements. Unlabeled active particles ($^0L_t^+$, $^0R_t^+$) will change apparent binding affinity and stoichiometry. The unlabeled and non-active particles ($^0L_t^-$, $^0R_t^-$) only shift the binding curves to lower affinities since they represent an overestimation of the total ligand and receptor concentrations. In the rest of this section we derive the concentrations of the different possible complexes that are formed by the interaction of ligands and receptors.

For the active particles, the probability of encountering a labeled or unlabeled active ligand/receptor is given by their mole fractions:

$$*p_L = \frac{*L_t^+}{*L_t^+ + {}^0L_t^+} \quad (9a)$$

$$^0p_L = \frac{{}^0L_t^+}{*L_t^+ + {}^0L_t^+} \quad (9b)$$

$$*p_R = \frac{*R_t^+}{*R_t^+ + {}^0R_t^+} \quad (9c)$$

$$^0p_R = \frac{{}^0R_t^+}{*R_t^+ + {}^0R_t^+} \quad (9d)$$

For $n_t$ ligand binding sites per receptor, the number of complexes with different ligands bound can be analytically calculated only for $n_t=1$ (Ref. 17). For $n_t \geq 2$ the concentration of bound complexes has to be numerically evaluated (see Tuk, B. and vanOostenbruggen, M. F., Trends Pharmacol. Sci. 17 (11), 403 (1996)). Numerical solutions were found in Mathematica (Version 5.0, Wolfram Research, Champaign, Ill.) by simultaneously solving these equations for equilibrium binding:

$$K_d = \frac{L_f^+ R_f^+}{RL}; K_d = \frac{L_f^+ RL}{RL_2}; \ldots; K_d = \frac{L_f^+ RL_{n_t-1}}{RL_{n_t}}; \quad (10a)$$

and

-continued $$R_t^+ = {}^*R_t^+ + {}^0R_t^+ = R_f^+ + \sum_{n=1}^{n_t}\binom{n_t}{n}RL_n \quad (10b)$$

$$L_t^+ = {}^*L_t^+ + {}^0L_t^+ = L_f^+ + \sum_{n=1}^{n_t}n\binom{n_t}{n}RL_n. \quad (10c)$$

Concentrations of total and free active ligands or receptors are denoted by $L_t^+$, $L_f^+$, $R_t^+$, and $R_f^+$, respectively. The binomial coefficient was introduced to account for the different possibilities how n ligands can bind to a receptor with $n_t$ binding sites. $RL_n$ are the concentrations of complexes containing n ligands. We assumed her that all binding sites on the receptor have the same $K_d$. The extension of the equations to different $K_d$s can be achieved by using different $K_d$s in Eqs. 10a. In addition, we demand that every ligand-receptor complex contains only one receptor but can possess several bound ligands. We thus exclude aggregation and oligomerization in this theory.

Assuming a receptor with $n_t$ possible binding sites and $n_b$ ($0 \leq n_b \leq n_t$) occupied binding sites, each of these sites can have either a fluorescent or a non-fluorescent active ligand as given by the probabilities of eqs. 9a and 9b. Each ligand-receptor complex can contain either a fluorescent or a non-fluorescent active receptor as given by the probabilities in eqs. 9c and 9d. The concentration of all active fluorescent receptors containing $n_b$ ligands of which $n^*$ are fluorescent (and $n = n_b - n^*$ are non-fluorescent) can thus be expressed by $$^*RL_{(n_b, n_*)} = \binom{n_t}{n_b}\binom{n_b}{n_*}{}^0p_L^{n_b-n^*} \cdot {}^*p_L^{n^*} \cdot {}^*p_R \cdot RL_{n_b} \quad (11)$$

The first binomial coefficient represents the number of possibilities to distribute $n_b$ ligands over $n_t$ binding sites. The second binomial coefficient is the number of possibilities to distribute $n^*$ fluorescent ligands over the $n_b$ occupied binding sites.

The concentration of all active non-fluorescent receptors containing $n_b$ ligands of which $n^*$ are fluorescent can thus be expressed by $$^0RL_{(n_b, n_*)} = \binom{n_t}{n_b}\binom{n_b}{n_*}{}^0p_L^{n_b-n^*} \cdot {}^*p_L^{n^*} \cdot {}^0p_R \cdot RL \quad (12)$$

We have thus calculated all concentrations necessary for the calculation of the CCF. The concentration $c_L$ of particles containing only ligand fluorophores which are not part of a ligand-receptor complex are given by $$c_L = {}^*L_t^- + \left({}^*L_t^+ - \sum_{n_b=1}^{n_t}\sum_{n_*=1}^{n_b}n_*({}^*RL_{(n_b,n_*)} + {}^0RL_{(n_b,n_*)})\right). \quad (13)$$

The second part on the right hand sides of Eq. 13 represents the unbound but active fluorescent ligands. The concentration $c_{Ln^*}$ of particles containing a non-fluorescent receptor and $n^*$ fluorescent ligands are given by $$c_{Ln^*} = \sum_{n_b=0}^{n_t} {}^0RL_{(n_b,n_*)} \quad (14)$$

The concentration $c_R$ of particles containing only receptor fluorophores which are not part of a ligand receptor complex are given by $$c_R = {}^*R_t^- + \left({}^*R_t^+ - \sum_{n_b=1}^{n_t}\sum_{n_*=1}^{n_b}({}^*RL_{(n_b,n_*)} + {}^0RL_{(n_b,n_*)})\right). \quad (15)$$

The second part on the right hand sides of Eq. 15 represents the unbound but active fluorescent receptors. The concentration $c_{RLn^*}$ of particles containing a fluorescent receptor and $n^*$ fluorescent ligands is given by $$c_{RLn^*} = \sum_{n_b=0}^{n_t} {}^*R_{(n_b,n_*)}. \quad (16)$$

These concentrations of particles with defined numbers of fluorophores can be used to calculate the CCF.

EXAMPLE

The Biotin-Streptavidin Ligand-Receptor System

The biotin-streptavidin ligand-receptor system is a well studied model system for ligand receptor interaction. In our case we use fluorescein labeled biotin (BF) and tetramethylrhodamine labeled streptavidin (TMRSA). There are several points in this system that considerably simplify the expression for the fluorescence intensity (Eq. 2) and thus the CCF (eqs. 3 and 4):

i) The fluorescence of TMRSA is not dependent on BF binding and no FRET was observed (data not shown). Thus all $\eta_{RLn^*i}$ are equal and can be written as $\eta_{Ri}$.

These two conditions lead to a simplification of Eq. 2:

$$F_i(t) = \eta_{Li}c_L + \sum_{n_*}\eta_{Ln^*i}c_{Ln^*} + \eta_{Ri}c_R + \sum_{n_*}(\eta_{Ln^*Ri} + \eta_{Ri})c_{RLn^*} \quad (17)$$

ii) The fluorescence of BF is quenched by 75% upon binding (see Gruber, H. J., Kada, G., Marek, M., and Kaiser, K., BBA-Gen. Subjects 1381 (2), 203 (1998); 20. Kada, G., Kaiser, K., Falk, H., and Gruber, H. J., BBA-Gen. Subjects 1427 (1), 44 (1999)), but it is not dependent on the number of BF ligands bound to TMRSA or unlabeled streptavidin. Thus, a complex with $n^*$ fluorescent ligands will have just $n^*$ times the fluorescence of a complex with only 1 fluorescent ligand. In addition, the quenching is the same in both detectors and can be described by the factor $q_L = 0.25$ (this implies that there is no shift in the emission spectrum of the ligand fluorophore). Therefore, $$\eta_{Ln^*i} = \eta_{Ln^*Ri} = n^* q_L \eta_{Li} \quad (18)$$

where the fluorescence yield of a BF molecules is denoted as $\eta_{Li}$. This leads to $$F_i(t) = \eta_{Li} c_L + \sum_{n_*} n_* q_L \eta_{Li} c_{Ln^*} + \eta_{Ri} c_R + \sum_{n_*} (n_* q_L \eta_{Li} + \eta_{Ri}) c_{RLn^*} \quad (19)$$

$$= \eta_{Li} c_L + \sum_{n_*} n_* q_L \eta_{Li} c_{Ln^*} + \eta_{Ri} c_R + \sum_{n_*} \eta_{Cn^*i} c_{RLn^*}.$$

To simplify the equations we defined here the fluorescence yield of the complexes with fluorescent receptor and n* fluorescent ligands:

$$\eta_{Cn^*i} = (n^* q_L \eta_{Li} + \eta_{Ri}) \quad (20)$$

Putting these equations into the CCF we get $$G_x(0) = \frac{\eta_{L1} \eta_{L2} c_L + \sum_{n^*} n_*^2 q_L^2 \eta_{L1} \eta_{L2} c_{Ln^*} + \eta_{R1} \eta_{R2} c_{R_v} + \sum_{n^*} \eta_{Cn^*1} \eta_{Cn^*2} c_{RLn^*}}{V_{\text{eff}} N_A \left[ \begin{pmatrix} \eta_{L1} c_L + \sum_{n^*} n_* q_L \eta_{L1} c_{Ln^*} + \\ \eta_{R1} c_R + \sum_{n^*} \eta_{Cn^*1} c_{RLn^*} \end{pmatrix}^* \begin{pmatrix} \eta_{L2} c_L + \sum_{n^*} n_* q_L \eta_{L2} c_{Ln^*} + \\ \eta_{R2} c_R + \sum_{n^*} \eta_{Cn^*2} c_{RLn^*} \end{pmatrix} \right]} \quad (21)$$

In our experiments the competitor (unlabeled biotin) has no influence on the fluorescence yields of the labeled particles ($\eta' = \eta$). For the negative control we thus have $$G_x^-(0) = \frac{\eta_{L1} \eta_{L2}^* L_t + \eta_{R1} \eta_{R2}^* R_t}{V_{\text{eff}} N_A (\eta_{L1}^* L_t + \eta_{R1}^* R_t)(\eta_{L2}^* L_t + \eta_{R2}^* R_t)}. \quad (22)$$

It should be noted that all assumptions can be verified directly from the intensity traces recorded in the two detection channels. The values $\eta_{Li}$, $\eta_{Ri}$, $\eta_{Cn^*i}$, and $q_L$ can be measured from samples by comparing the signals in the two detectors. The concentrations $c_L$, $c_{Ln^*}$, $c_R$, and $c_{RLn^*}$ can be numerically calculated from eqs. 13-16 in dependence on the total receptor and ligand concentrations. As fitting parameters we have thus left the $K_d$, the effective observation volume $V_{\text{eff}}$ and the relative concentrations of fluorescent and non-fluorescent receptors and ligands.

The CCF of Eq. 21 contains several contributions: 1) The first three sums in the numerator are contributions of particles that contain either only ligand fluorophores or only receptor fluorophores. These contributions are similar to the autocorrelation of these particles and are caused by the cross talk of the signal into both detectors. 2) The fourth sum in the numerator is the contribution of particles that actually contain both fluorophores of ligands and receptors and represent actual binding interactions. The contribution of the different particles depends solely on the product of their fluorescence yields in the two detectors. Thus the condition for a successful distinction between the different contributions to the CCF is only that $\eta_{Cn^*1} \eta_{Cn^*2}$ is sufficiently different from $\eta_{L1} \eta_{L2}$, $\eta_{R1} \eta_{R2}$, and $n^{*2} q_L^2 \eta_{L1} \eta_{L2}$. This implies that even when the same label is used on both ligand and receptor, a distinction is possible between the different contributions to the CCF, provided that the fluorescence characteristics of the complex are different from the characteristics of the ligand and receptor alone (see P. Schwille, *Cross-Correlation Analysis in FCS*, E. L. Elson and R. Rigler (Springer, Berlin, 2001) Chap. 17, pp. 360-378).

The negative control can be fit to Eq. 22 and can be used to determine $V_{\text{eff}}$. And with the knowledge of the total ligand and receptor concentrations $L_t$ and $R_t$ the positive control can be fit with 7 independent parameters including the receptor and ligand impurities (eqs. 8a and 8b) and the $K_d$. Different models with different number of binding sites can be obtained by using different values of $n_r$. If the binding sites have in addition different $K_d$s this can be put into eqs. 10 thus increasing the number of fit parameters.

Since we have shown that the invention can be as well used with standard organic dyes the extension of the two-color setup to n-color schemes is straightforward, as depicted in FIG. 4. To split the signal in different detection channels one can use dispersive elements or wavelength selective filters and mirrors. All data treatment can then be done as described above.

It is also possible to extend the calculations to higher order correlation functions or to simple coincidence analysis where only parts of a correlation function are calculated.

Using the measurement apparatuses of FIG. 2 or 4, combined with the theoretical basis discussed above, it becomes possible to determine what factors influence the CCF and find out the sensitivity of the CCF of various fluorophores.

Figure 5A:
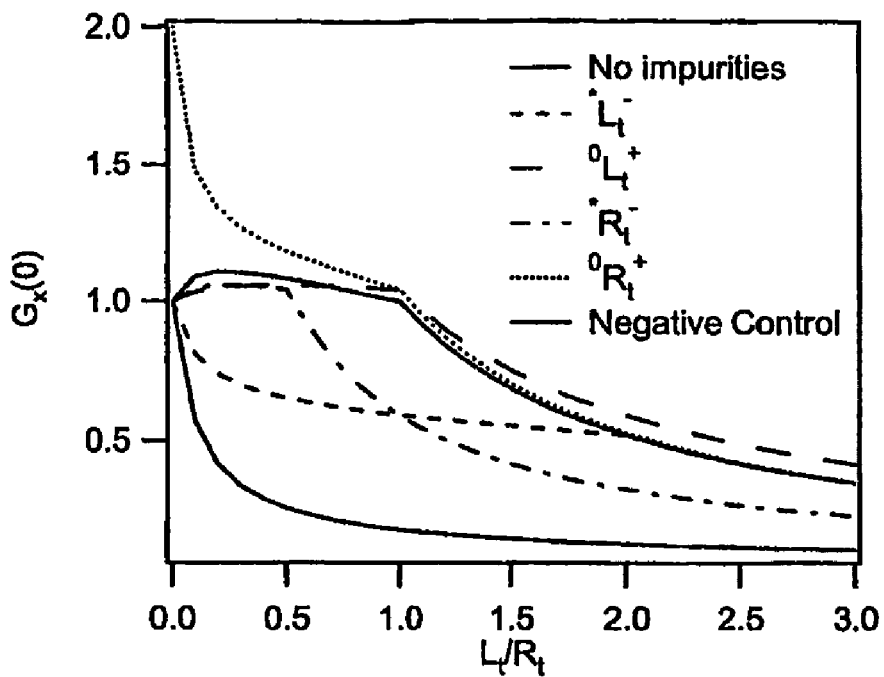
FIGS. 5A and 5B show the influence of impurities on the cross-correlation function (CCF) in an example embodiment.
Figure 5B:
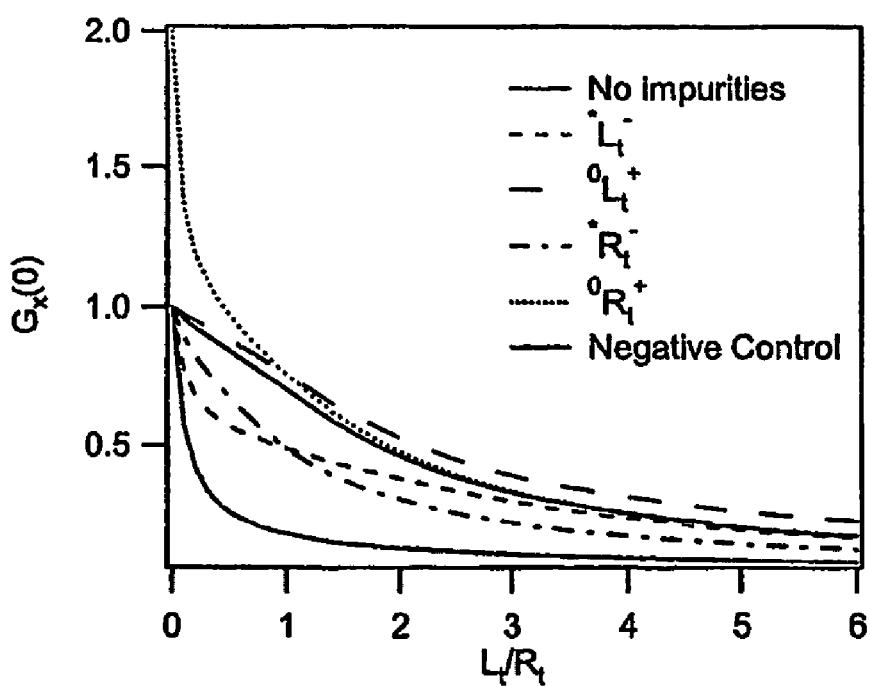

FIGS. 5A and 5B show the Influence of impurities on the CCF. The amplitude of the CCF is shown versus the ligand to receptor concentration ratio. The two FIGS. 5A and 5B show the simulations/calculations for different affinities of the binding partners. A: dissociation constant Kd=$10^{-15}$ nM; B: dissociation constant Kd=$10^{-9}$ nM. The curves were calculated for a standard fluorophores pair (fluorescence yields $\eta_{L1}$=27000 Hz, $\eta_{L2}$=3000 Hz, $\eta_{R1}$=3000 Hz, $\eta_{R2}$=27000 Hz; binding stoichiometry 1:1; no quenching of ligand and receptor $q_L$=$q_R$=1) for different impurities at two different $K_d$s: A) $K_d$=$10^{-15}$ M, B) $K_d$=$10^{-9}$ M.

Figure 6:
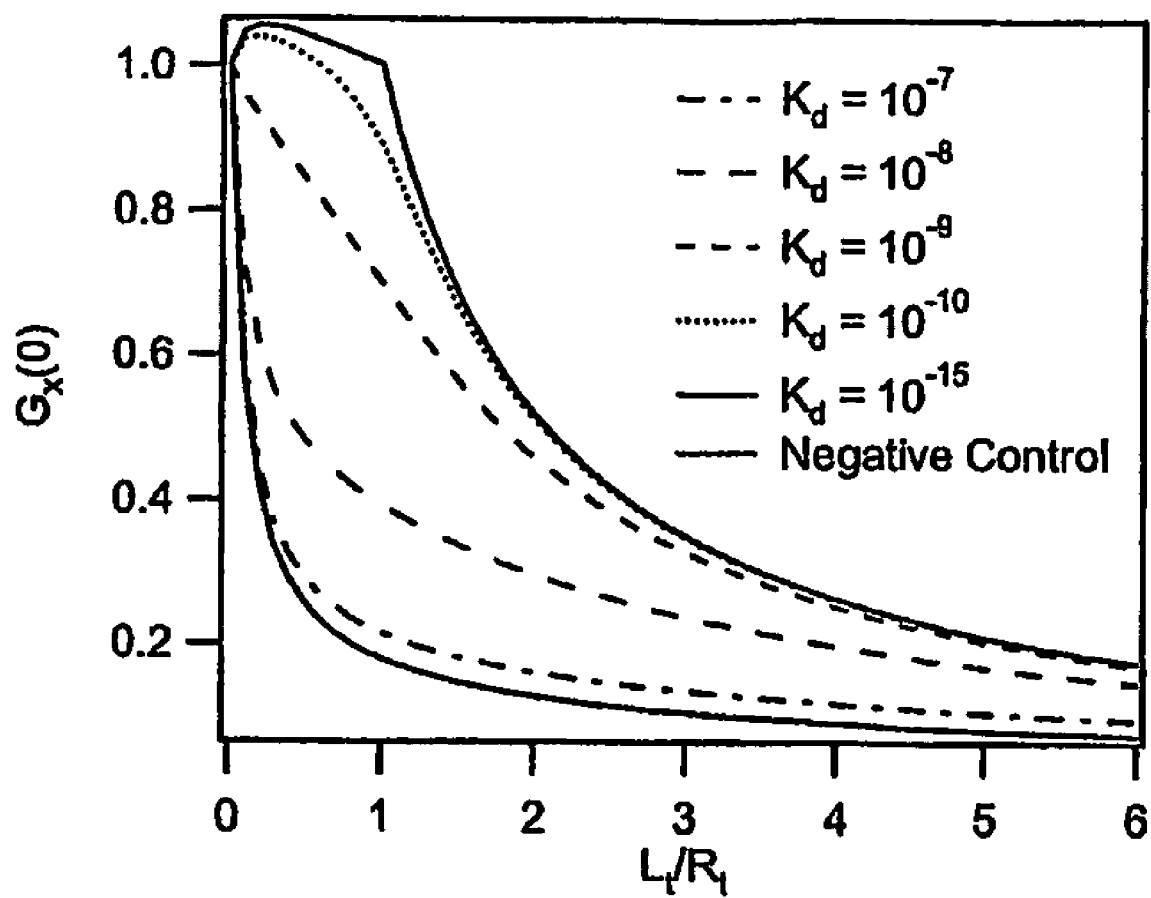
FIG. 6 shows the influence of Kd on the CCF in an example embodiment.

FIG. 6 shows the Influence of the $K_d$ on the CCF. The amplitude of the CCF is shown versus the ligand to receptor concentration ratio. The curves were calculated for a standard fluorophore pair (fluorescence yields $\eta_{L1}$=27000 Hz, $\eta_{L2}$=3000 Hz, $\eta_{R1}$=3000 Hz, $\eta_{R2}$=27000 Hz; binding stoichiometry 1:1; no quenching of ligand and receptor $q_L$=$q_R$=1).

Figure 7:
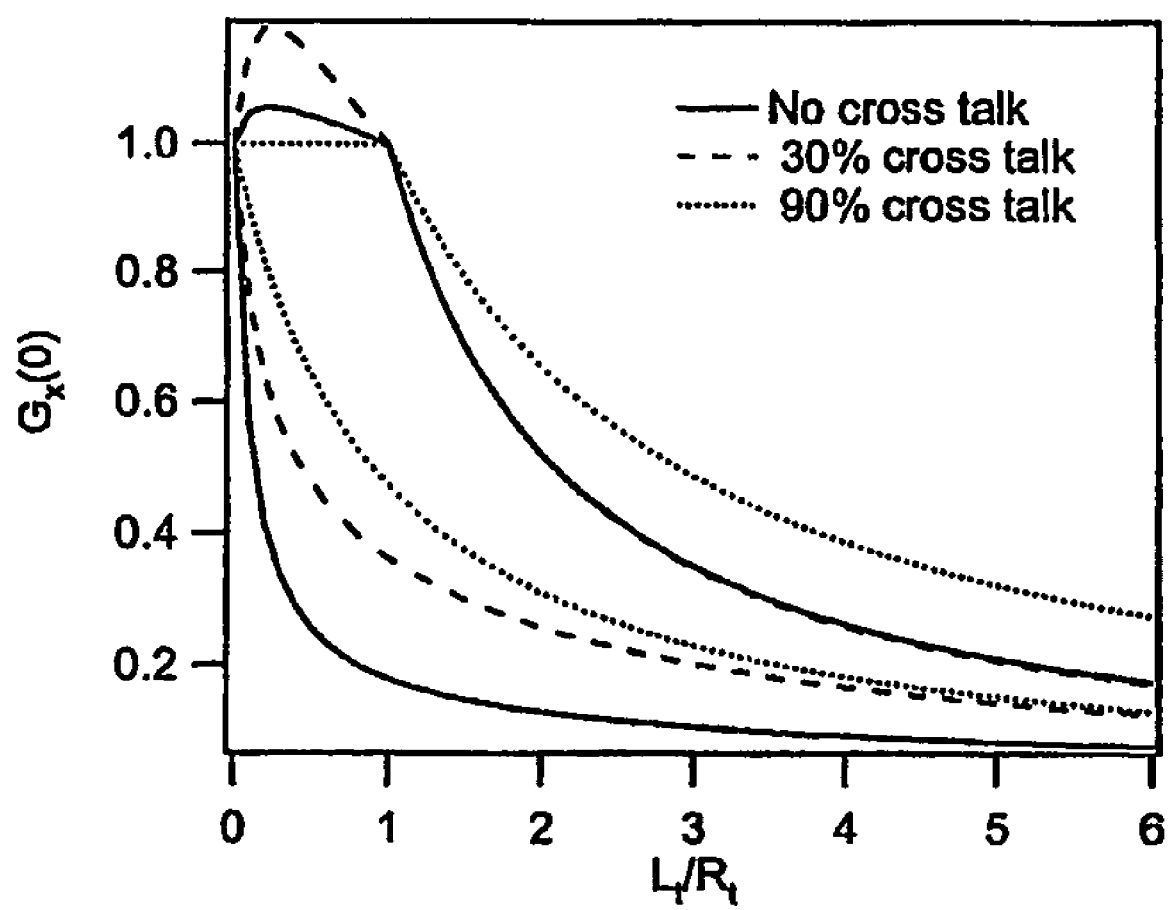
FIG. 7 shows the influence of the cross-talk on the CCF in an example embodiment.

FIG. 7 shows the Influence of cross talk on the CCF. The amplitude of the CCF is shown versus the ligand to receptor concentration ratio. The curves were calculated for three different levels of cross talk of the ligand fluorophores into the channel of the receptor fluorophores (fluorescence yield $\eta_{L1}$+$\eta_{L2}$=30000 Hz distributed over the two channels depending on cross talk). The receptor fluorophores was assumed to have a cross talk of 10% into the first channel ($\eta_{R1}$=3000 Hz, $\eta_{R2}$=27000 Hz;). The binding stoichiometry is 1:1 and no quenching of ligand and receptor were used $q_L$=$q_R$=1.

Figure 8A:
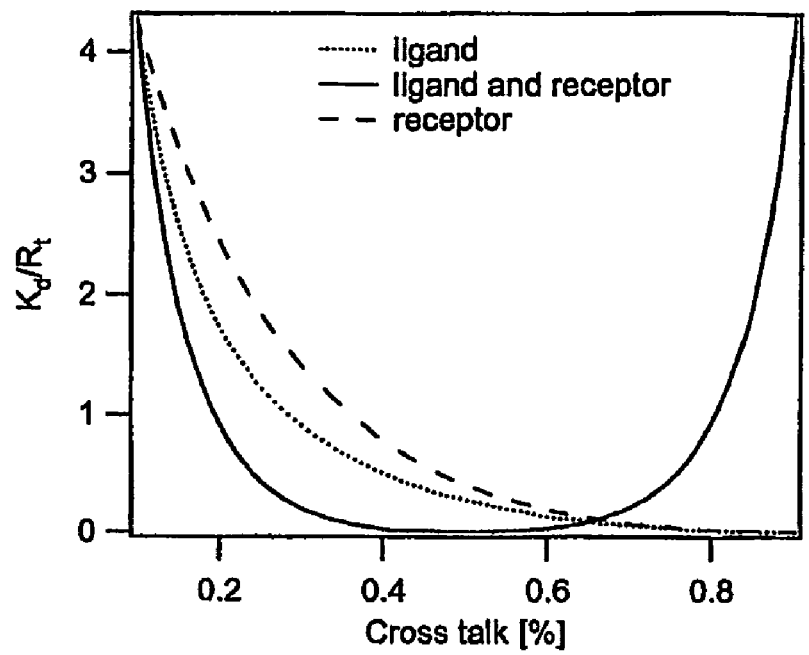
FIGS. 8A and 8B shows the influence of increasing cross-talk of ligand fluorophores on sensitivity in an example embodiment.
Figure 8B:
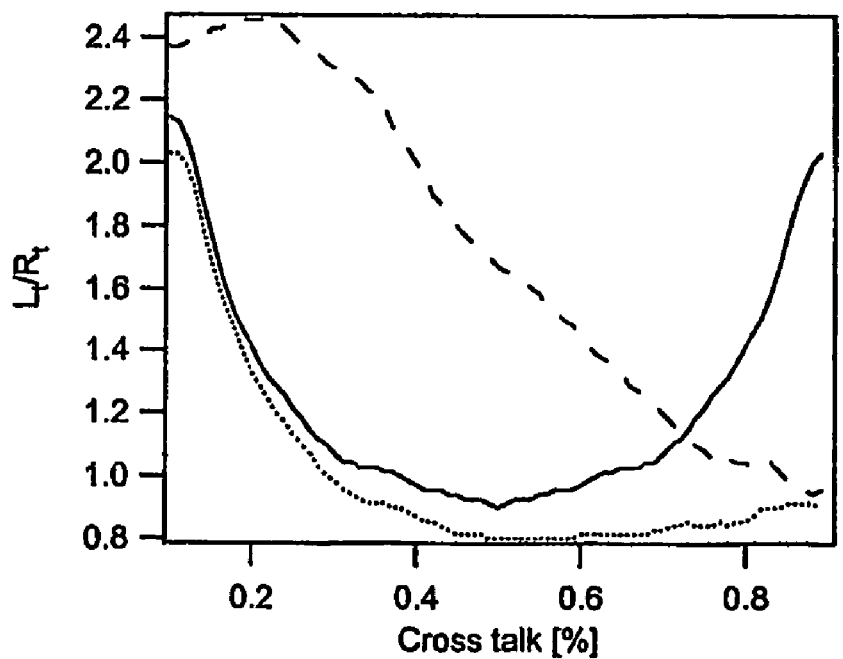

FIGS. 8A and 8B show the sensitivity of SW-FCCS depending on increasing cross talk of ligand fluorophores (dotted lines), receptor fluorophores (dashed lines), or both fluorophores simultaneously (solid lines). For these calculations a 1:1 binding stoichiometry and no quenching upon binding were assumed. For the ligand and receptor curves the cross talk of one fluorophore was fixed at 10% while the cross talk of the other fluorophore was varied between 10 and 90%. For the ligand and receptor curves the cross talk of both fluorophores was varied simultaneously between 10 and 90%. The fluorophores were assumed to result in 30000 counts per second and particle over all detection channels. For FIG. 8A, the values of $K_d$/$R_t$ are depicted versus percentage of cross talk. In FIG. 8B, the values of $L_t$/$R_t$ are depicted versus percentage of cross talk. Maximum measurable $K_d$s can be calculated from the data according to Eq. 7.

Table 1 shows the Fluorescence yields of the different particles in the detection channels 1 and 2. Fluorescence yields and their products for ligands and receptors are denoted by $\eta_{X1}$, $\eta_{X2}$, $\eta_{X1}\eta_{X2}$, respectively (X stands for L, ligand, or R, receptor, depending of the role of the molecule). The residual fluorescence after binding for the different particles is given by $q_X$. The fluorescence yield product for the ligand-receptor complexes is given by $\eta_{C1}\eta_{C2}$.

TABLE 1

| Molecule | $\eta_{X1}$ [Hz] | $\eta_{X2}$ [Hz] | $q_X$ | $\eta_{X1}\eta_{X2}$ [$10^6$ Hz$^2$] | Complexes | $\eta_{C1}\eta_{C2}$ [$10^6$ Hz$^2$] |
|---|---|---|---|---|---|---|
| BF | 25245 | 520 | 0.25 | 13.1 | — | — |
| TMRSA | 27540 | 1670 | 1.0 | 46.0 | BF-TMRSA | 60.9 |
| QR | 6965 | 74995 | 1.0 | 522.3 | BF-QR | 1006.1 |
| QD | 3082 | 120704 | 1.0 | 372.0 | BF-QD | 1149.0 |

BF - Biotin-fluorescein
TMRSA - tetramethylrhodamine
QR - Quantum Red
QD - Semiconductor Nanocrystal Table 2 shows the maximum $K_d/R_t$ values with corresponding $L_t/R_t$ values, for a value of the detection threshold R=1. Values are given for Flu/QR and Flu/TMR pairs of fluorophores. With these values maximum and minimum detectable $K_d$s can be calculated by Eq. 7. All values were calculated using the spectroscopic data of Table 1 and using Eq. 18. Note that for the Flu-TMR system for a 1:1 binding stoichiometry and 20% fluorescent non-active impurities detection of binding is not possible. Therefore, the numbers for 10% ligand and receptor impurities are given.

By including several detectors or an imaging detector the detected wavelength range can be controlled and different wavelength ranges can be detected simultaneously and their mutual auto- and cross-correlations can be determined.

Figure 9:
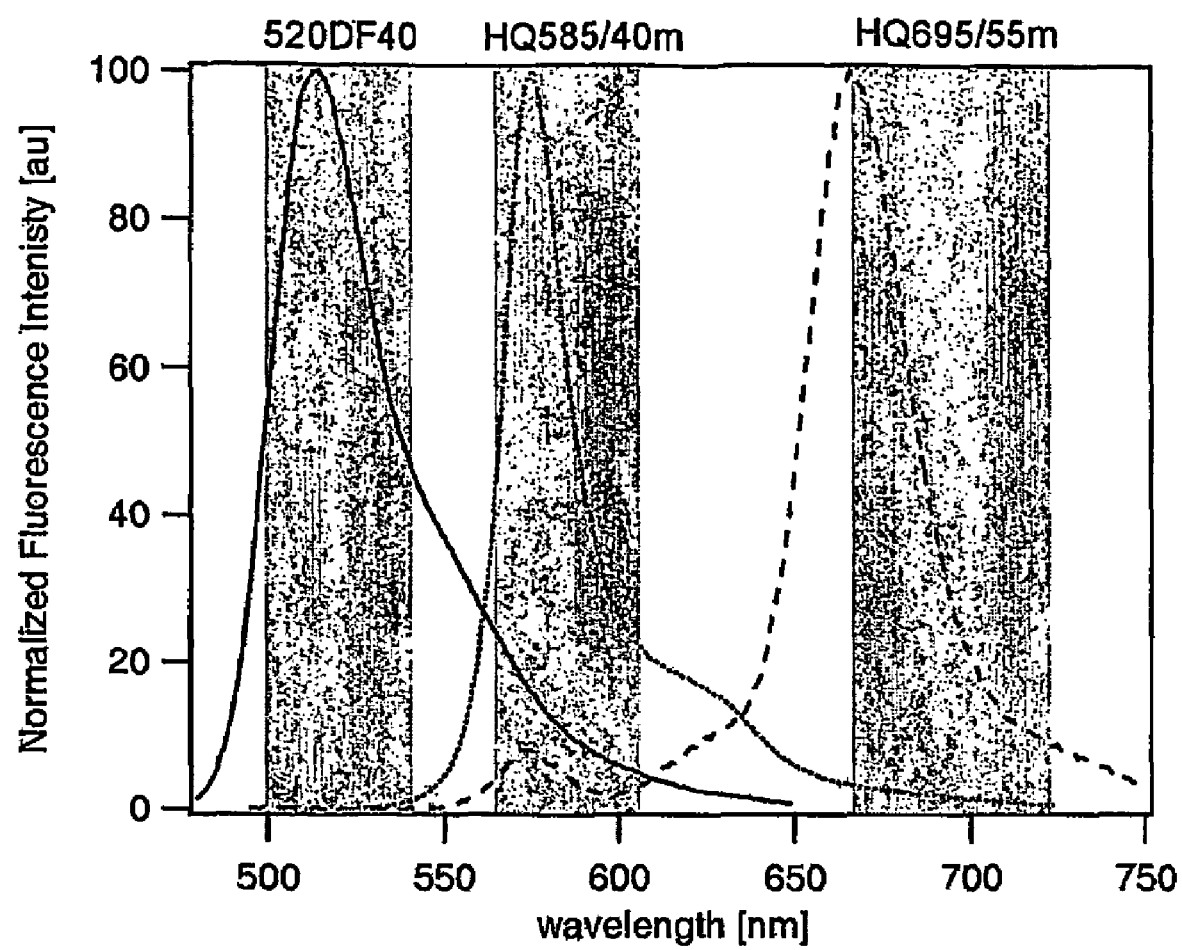
FIG. 9: shows spectra of the probes used for three color detection by single laser line excitation, in an example embodiment.

FIG. 9: shows spectra of the probes used for three color detection by single laser line excitation: biotinfluorescein (BF, solid line), R-phycoerythrin biotin-XX conjugate (BPE, dotted line), and Alexa Fluor 647-R-phycoerythrin streptavidin (AX, dashed line). Indicated as gray squares are as well the transmission ranges at full width half maximum of the bandpass filters used to detect the probes in the different detectors: 520DF40 (Omega), HQ585/40m (Chroma), HQ695/55m (Chroma).

Figure 10:
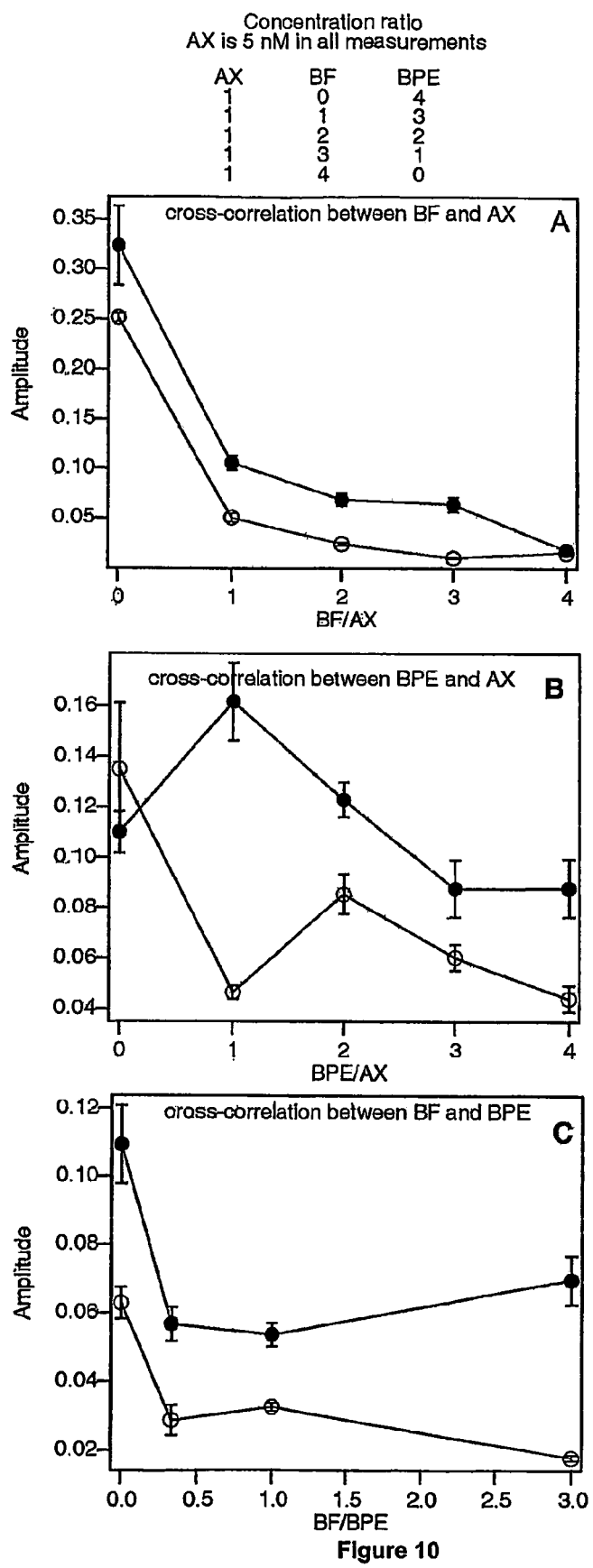
FIGS. 10 A to C show results of proof of principle measurements of single laser-line one-photon excitation of three fluorophores in an example embodiment.

FIG. 10 A to C show results of proof of principle measurements of single laser-line one-photon excitation of three fluorophores and the detection of their mutual cross correlations. Higher correlations can as well be calculated if necessary (reference is made to K. G. Heinze, M. Jahnz, P. Schwille. Triple Color Coincidence Analysis One Step Further in Following Higher Order Molecular Complex Formation. Biophys. J. 86, 506-516, 2004). In this example the following labeled samples are used: Alexa Fluor 647-R-phycoerythrin streptavidin (AX), biotin fluorescein (BF), R-phycoerythrin biotin-XX conjugate (BPE). The measurements were conducted with a concentration of 5 nM for AX, and different concentrations of BF and BPE which are given as multiples of AX concentration in the table shown above FIG. 10A.

Cross-correlation between A) BF and AX, B) BPE and AX, and C) BF BPE. All figures show the case of binding (full circles) and the case of inhibited binding by excess of unlabeled biotin (empty circles). In all cases can the cross correlation due to binding be detected against the negative control, i.e. the empty circle graphs in FIG. 10 A to C.

TABLE 2

| Stoichiometry | No quenching, no impurities | | 80% quenching of ligand (green) | | 80% quenching of receptor (red) | | Rec. imp. 20%, Lig imp. 20% | |
|---|---|---|---|---|---|---|---|---|
| | $L_t/R_t$ | $K_d/R_t$ | $L_t/R_t$ | $K_d/R_t$ | $L_t/R_t$ | $K_d/R_t$ | $L_t/R_t$ | $K_d/R_t$ |
| fluorescein/quantum-red | | | | | | | | |
| 1:1 | 41 | 43.5 | 1.99 | 0.77 | 39.2 | 9.0 | 33 | 22.0 |
| 1:2 | 118 | 175.4 | 15 | 9.9 | 76.0 | 63.2 | 97.0 | 102.6 |
| 1:4 | 113 | 377 | 33 | 33 | 85.0 | 153.0 | 104.0 | 224.0 |
| fluorescein/tetramethylrhodamine | | | | | | | | |
| 1:1 | 0.920 | 0.009 | 0.996 | 0.002 | 0.985 | 0.003 | 1.025* | 0.0004* |
| 1:2 | 1.2 | 1.4 | 1.0 | 0.18 | 1.1 | 0.87 | 1.0 | 0.54 |
| 1:4 | 5.3 | 4.2 | 2.3 | 1.3 | 4.2 | 3.3 | 3.5 | 2.2 |

*for 10% impurities since for 20% impurities binding cannot be detected anymore.

The invention allows the measurement of FCCS with a single laser beam for excitation by using fluorophore combinations with similar excitation wavelength but different Stokes shifts to allow the excitation of the fluorophores with a single laser wavelength and the separation of the emitted fluorescence signal. We propose two large Stokes shift fluorophore types (fluorescence energy transfer dyes and quantum dots) that can be used for this purpose. In addition, measurements show that the invention can be as well extended to other fluorophores (e.g. small organic fluorophores) which have smaller Stokes shift but whose emission can be distinguished in at least two wavelength selective channels.

Applications of the invention can be found in the life sciences and especially in high-throughput screening applications (e.g. drug discovery). Discovery of interaction partners in biology, pharmacology, and medicine rely on the detection of binding events between two particles (e.g. drug and target, two interacting proteins). With conventional FCS this is only possible when the two binding partners have a mass difference of a factor 8-10. FCCS is independent of mass differences and detects specifically binding interactions. Since measurements can be done in the second range high-throughput screening is possible with this technique.

The invention can extend in general to dyes with different emission maxima, whose emission in different wavelength selective channels can be distinguished, in combination with the installation of several detectors in the detection path, allows measurements of more than just 2 fluorophores in a system provided all fluorophores can be excited at the same wavelength and detected in different detection channels. Therefore, a fluorophore pair or 3 or more fluorophores can be used in the system. Also, the dyes can be standard organic dyes, fluorescent energy transfer dyes, or other suitable dyes. Thus the interaction of several different molecules can be measured simultaneously.

Typically, for the measurement of interactions, all interacting partners have to be fluorescently labeled. Labeling of interaction partners can change their binding characteristics. This is encountered also for the conventional FCS, FCCS and other fluorescence techniques. Embodiments of the invention may be used for lead discovery. The leads can then be more thoroughly tested.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

What is claimed is:

1. A screening method for at least two binding partners, which comprises:
    labeling each binding partner with a fluorophore, characterized in that the at least two fluorophores have substantially the same single-photon excitation wavelength and different emission wavelengths;
    detecting emission signals from the respective fluorophores at the different respective emission wavelengths; and
    processing the detected emission signals to obtain fluorescence correlation spectroscopic data for screening the binding partners.

2. The method of claim 1, wherein one of the fluorophores has as a larger Stokes shift than the other.

3. The method of claim 2, characterized in that a relative Stokes shift difference between the fluorophores is greater than about 50 nm.

4. The method of claim 3, characterized in that the relative Stokes shift difference between the fluorophores is greater than about 100 nm.

5. The method of claim 1, characterized in that at least one of the fluorophores comprises a nanocrystal or a quantum dot.

6. The method of claim 1, characterized in that at least one of the fluorophores comprises a fluorescent energy transfer dye.

7. The method of claim 1, characterized in that at least one of the fluorophores comprises a standard organic dye.

8. The method of claim 1, characterized in that the fluorophores comprise fluorescein and quantum red.

9. The method of claim 1, characterized in that the fluorophores comprise fluorescein and tetramethylrhodamine.

10. The method of claim 1 characterized in that the fluorophores comprise fluorescein and semiconductor nanocrystals.

11. The method of claim 1, characterized in that the fluorophores comprise 3 or more fluorophores.

12. The method of claim 1, characterized in that the binding partners have a mass difference of less than a factor of 10.

13. The method of claim 12, characterized in that the binding partners have a mass difference of less than a factor of 8.

14. The method of claim 1, characterized in that the binding partners comprise biotin and streptavidin.

15. A biological screening apparatus for screening at least two binding partners, the system comprising:
    a single laser beam source;
    an optical system for directing the single laser beam onto the binding partners and for directing fluorescence emitted from the sample towards a spectrograph unit, wherein the fluorescence is emitted from at least two fluorophores labeled to different ones of the binding partners, the fluorophores having substantially the same single-photon excitation wavelength and different emission wavelengths;
    the spectrograph unit separating the emitted fluorescence by wavelength;
    a detector unit for detection of the fluorescence at respective different wavelengths; and
    a processing unit for obtaining fluorescence correlation spectroscopic data for screening the binding partners.

* * * * *